United States Patent [19]

McCabe et al.

[11] Patent Number: 5,833,642

[45] Date of Patent: Nov. 10, 1998

[54] ABSORBENT PRODUCT

[75] Inventors: John P. McCabe, North Yorkshire, United Kingdom; Peter J. Stevens, Colleyville, Tex.

[73] Assignee: Johnson & Johnson Medical, Inc., Arlington, Tex.

[21] Appl. No.: 825,834

[22] Filed: Apr. 4, 1997

Related U.S. Application Data

[60] Continuation of Ser. No. 495,732, Jun. 8, 1995, abandoned, which is a division of Ser. No. 274,658, Jul. 13, 1994, Pat. No. 5,716,337, which is a continuation of Ser. No. 68,354, May 27, 1993, abandoned.

[30] Foreign Application Priority Data

Jun. 10, 1992 [GB] United Kingdom ............... 9212303
Jul. 31, 1992 [GB] United Kingdom ............... 9216285

[51] Int. Cl.⁶ ............................. A61F 15/00; A61F 13/00
[52] U.S. Cl. ................................. 602/43; 602/49; 602/59; 604/304
[58] Field of Search ................... 602/41–59; 604/364, 604/368, 385.1, 304, 307, 56, 82, 92, 410, 414

[56] References Cited

U.S. PATENT DOCUMENTS

| | | |
|---|---|---|
| 3,095,877 | 7/1963 | Rowan . |
| 3,595,235 | 7/1971 | Jespersen . |
| 3,762,413 | 10/1973 | Hanke . |
| 3,814,101 | 6/1974 | Kozak . |
| 4,460,642 | 7/1984 | Errede et al. . |
| 4,793,337 | 12/1988 | Freeman et al. . |
| 5,000,746 | 3/1991 | Meiss . |
| 5,002,814 | 3/1991 | Knack et al. . |
| 5,180,622 | 1/1993 | Berg et al. . |
| 5,197,945 | 3/1993 | Cole et al. . |
| 5,470,625 | 11/1995 | Derrault ........................ 602/48 X |

FOREIGN PATENT DOCUMENTS

| | | |
|---|---|---|
| 0 171 268 | 12/1986 | European Pat. Off. . |
| 0 344 913 | 6/1989 | European Pat. Off. . |
| 2 402 594 | 6/1979 | France . |
| 1 642 146 | 4/1971 | Germany . |

*Primary Examiner*—Linda C. M. Dvorak
*Assistant Examiner*—Kim M. Lee
*Attorney, Agent, or Firm*—Andrew C. Farmer

[57] ABSTRACT

A product suitable for absorbing wound exudate comprising a series of interconnected square or rectangular perforated bags made of a substance of maximum thickness 1 mm e.g. film, which is substantially non-adherent to a wound, wherein alginic acid or a salt thereof such as calcium alginate is housed in the bags, preferably in the form of small spheres. The film preferably comprises ethylene/methyl acrylate copolymer. Alternatively, the product comprises a string along which beads of alginic acid or alginate are threaded.

17 Claims, 1 Drawing Sheet

ABSORBENT PRODUCT

This is a continuation of application Ser. No. 08/495,732, filed Jun. 8, 1995, abandoned, which is a division of application Ser. No. 08/274,658, filed Jul. 13, 1994, U.S. Pat. No. 5,716,337, which is a continuation of application Ser. No. 08/068,354, filed May 27, 1993, abandoned.

This invention relates to a product suitable for absorbing fluid from wounds during the healing process.

Various products have been used for absorbing fluids such as wound exudate, but they tend to be fibrous and are therefore prone to adhere to the wound and to leave bits in the wound.

Such difficulties have been overcome by the use of the absorbent product of this invention. This product comprises bits of alginic acid or a salt thereof as an assemblage capable of being applied to the vicinity of a wound to absorb the wound exudate. The form in which the bits are assembled is a string on which the bits are carried directly or perforated bags interconnected by a string in which the bits are housed, which bags are made of a substance of maximum thickness 1 mm which is substantially non-adherent to a wound.

Bits can take various forms. Thus, they can be granules, pellets, spheres or in one specific form beads, i.e. spheres having a hole therethrough, so that they can be strung together. In general, by bit we mean any small discrete quantity which need not be regular in shape and this quantity is usually less than 0.1 gm in weight.

Alginic acid or a salt thereof (hereinafter referred to as "alginate") is extracted from seaweed and consists of linear polysaccharides in which the monomeric units are mannuronic acid and guluronic acid. The alginate which is used may, for example, be calcium alginate, zinc alginate, sodium alginate, barium alginate, ammonium alginate or mixtures thereof. Calcium alginate is particularly preferred and may be prepared by an ion exchange reaction between sodium alginate and calcium chloride.

The alginate may however be in the form of a gel, generally from 0.01 to 2.0 mm in thickness. Such gels may suitably be formed by the controlled introduction of a suitable cation (e.g. calcium) into a solution of a water soluble alginate such as sodium alginate, preferably in the presence of a pH modifier such as glucono delta lactone. The alginate concentration may be, for example, from 2% to 20% by weight and the final cation concentration may suitably be from 0.2% to 10% by weight. The resultant gel will typically contain from 30% to 99% by weight of water, and it may then be partially or completely dried if desired, e.g. to a water content of from 15% to 50%, and more preferably from 20% to 40% by weight.

The assemblage of bits can be of various constructions. Thus, in one form the bits of alginate are housed in a perforated bag made of a thin substance so that in use the exudate from the wound passes through the perforations where it is absorbed by the alginate, for example as pellets, spheres or granules which thereby swell when absorbing the exudate.

In another form the assemblage comprises a string along which beads of alginate are threaded. A suitable length of the string is then placed adjacent to the wound and when the exudate is absorbed by the beads they swell.

In all cases the assemblage is preferably sterile packaged.

When the alginate is housed in a perforated bag the substance from which the bag is made should be of maximum thickness 1 mm, preferably less than 0.5 mm. The substance should also be substantially non-adherent to a wound.

Although the alginate can be housed in just one perforated bag it is preferred that it be housed in a series of interconnected perforated bags.

The bag or bags are preferably made of a film, i.e. any suitable material of thickness less than 300 micrometers, for example from 20 to 100 micrometers thick, and preferably from 30 to 70 micrometers thick, e.g. about 60 micrometers.

Each bag which contains alginate should be perforated. These perforations should be of sufficient size to allow wound exudate to penetrate, but not so large that substantial portions of the alginate can drop out of the bag. Preferably the alginate is used in the form of small dry spheres, and particularly spheres having a diameter of 0.5 mm to 1.5 mm, for example 1 mm. By "sphere" we do not mean that it has to be a geometrically perfect sphere and could include granules if not too irregular.

The perforations in the bags should have dimensions less than the diameter of such spheres. Typical perforations are squares with sides of 0.5 to 1.00 mm length, e.g. about 0.8 mm.

The amount of alginate in each bag can vary but amounts of from about 1.5 mg to 100 mg per bag are suitable. When the alginate is in the form of spheres each bag preferably has from 1 to 50 spheres, especially from 28 to 32 spheres, e.g. 30 spheres.

The shape of the bags can vary but preferred are substantially rectangular or square bags, preferably of 1 to 5 cm width and 1 to 10 cm length, especially with a width 2 to 3 cm, and length 3 to 4 cm. The depth is preferably about 0.1 cm to 0.4 cm when the alginate is dry.

Alternatively cylindrical bags can be used of length preferably from 1 to 10 cm, especially from 3 to 4 cm. As another alternative, the bags can be for example elliptical cylinders. The diameter of cylindrical bags (or the maximum diameter if the bags are of elliptical section) is preferably from 1 to 5 cm, and more preferably from 2 to 3 cm.

Preferably the series of bags comprises a series of contiguous bags, but this is not essential. The bags are preferably joined to each other side by side, so that the series or line of bags resembles one long flat ribbon. This ribbon is preferably 5 to 30 cm in length and 0.5 to 2.5 cm width.

It is preferred that the bags be connected with a string, thread or cord or similar line running substantially along the length of bags and such a line, e.g. string, thread or cord, is essential when the bags are adjacent to one another but not contiguous with one another. In this case it connects the bags together. Preferably the line runs through each bag and if for example the bags are a series of end-on cuboids or cylinders, the line can run substantially centrally through each cuboid or cylinder, i.e. centrally throughout the length of the ribbon.

The bag or bags must be made of a substance which is substantially non-adherent to the wound, i.e. substantially hydrophobic. Various plastic substances can be used but the preferred plastics is one comprising ethylene/methyl acrylate copolymer and preferably including low density polyethylene. One preferred form comprises 16% by weight of ethylene/methyl acrylate copolymer, 83% by weight low density polyethylene and 1% process additives.

Other suitable plastics materials include water-impermeable polymers, such as a polyolefin. Polyethylene and polypropylene are representative examples of this class, but polymers of higher olefins may of course be used, as may copolymers of two or more olefins, or copolymers of the olefin and one or more other monomers.

Although fibrous plastics material is not preferred because of the risk of portions adhering to the wound it is possible to use such substances if the fibres are fully bonded to one another and there are no loose fibres.

Examples of such fibrous materials which may be used are polyolefins such as polyethylene, polypropylene and polybutylene homopolymers and copolymers, vinyl polymers such as polyvinylchloride, polyamides such as nylon, and polyesters. Other fibres include rayon and acrylic fibres. In particular one can use polyester fibres having a relatively high melting point of approximately 250° C.

To use this form of the product the series of bags, preferably in the form of a ribbon, is fed into the wound.

Whilst present in the wound, the alginate preferably as dried spheres, absorbs fluids such as wound exudate, and the alginate if in the form of spheres will swell to produce spheres of diameters of approximately 1 to 3 mm, e.g. about 3 mm. When all the wound exudate has been absorbed the series of bags, e.g. ribbon, now containing hydrated alginate, will be removed and discarded.

When the assemblage comprises a string along which beads of alginate are threaded, the string can be the same or similar to that described above in connection with the bags. The string can be a thin length of cord, thread, twine, fibre or similar material and may be of natural or synthetic material. Thus it may be a nylon thread.

If the beads are spaced at intervals along the string it is preferred that the diameter of the holes in the beads is such that the beads are not too free to slide along the string so that the beads remain spaced apart. A string or fairly course twine having a fairly rough surface, would also be of assistance in this respect. When the beads are spaced apart it is preferred that the average spacing is about the diameter of the bead, e.g. about 3 mm.

If desired the string of beads may be contained in a housing made of thin perforated material. This housing is preferably cylindrical and which preferably houses substantially the whole string of beads. The perforated material from which the housing is made is preferably that described and exemplified above in connection with the perforated bags. In this case however it is not necessary that the perforations are smaller than the diameter of the beads. As before the preferred material for the housing is a plastics comprising ethylene/methyl acrylate copolymer and low density polyethylene.

Also according to this invention, the alginate especially in the form of granules, pellets or spheres may be sprinkled onto the wound to absorb the exudate. They would be allowed to rehydrate before being irrigated away.

In a further embodiment the bits of alginate, e.g, spheres of alginate, could contain active wound healing agents, for example growth factors, collagen, glycosaminoglycans, vitamins, antiseptic agents and enzyme debriders.

The advantages of the product of the invention are that it can be completely removed and it is non-adherent. Prior art products tend to be fibrous and are therefore prone to adherence and to leave bits of fibre in the wound.

Specific forms of the invention are described with reference to the drawings in which.

Figure 1:
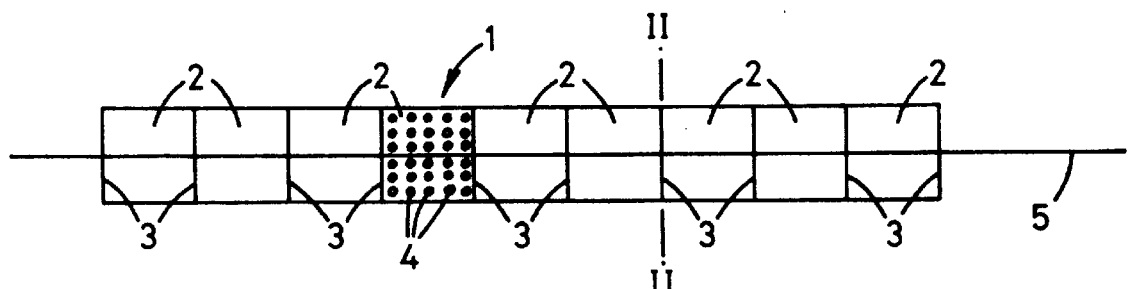
FIG. 1 shows one form of the invention as a section of a ribbon along line I—I of FIG. 2.
Figure 2:
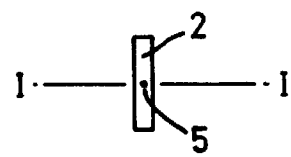
FIG. 2 is a cross-sectional view of the ribbon along line II—II of FIG. 1.

Referring to FIGS. 1 and 2, 1 indicates a series of rectangular contiguous bags 2 sealed at edges 3. Each bag is made of plastics film comprising ethylene methyl/acrylate copolymer and low density polyethylene and each bag is perforated with perforations 4 as shown on one of the bags.

Each bag contains approximately 56 mg of calcium alginate spheres of diameter less than or approximately equal to 1 mm when dry. A string 5 runs through each of the bags to facilitate entry and removal of the ribbon from the wound. When the spheres absorb exudate they swell to a diameter of about 3 mm.

Figure 3:
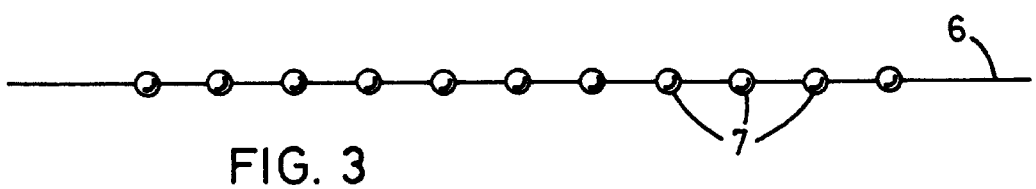
FIG. 3 shows another form of the invention.

Referring to FIG. 3 beads of alginate 7 of approximate diameter 3 mm are threaded onto a string 6 at intervals of approximately 4 mm.

Figure 4:
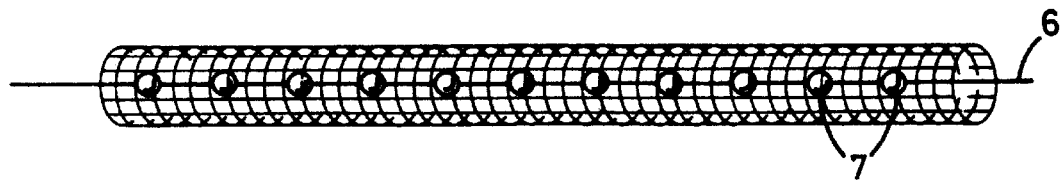
FIG. 4 shows a modification of the invention shown in FIG. 3.

Referring to FIG. 4 the string of beads as shown in FIG. 3 is housed in a perforated cylinder made of the same material as used to make the bags shown in FIGS. 1 and 2. The perforations are squares of sides approximately 2 mm.

When placed adjacent to a wound the beads of the string of FIG. 3 or of the housed string of FIG. 4 swell as they absorb the exudate.

What is claimed is:

1. A method for absorbing exudate from a wound comprising the steps of:

connecting in a linear, elongate series a plurality of absorbent members of alginic acid or a salt thereof, along a flexible, linearly elongated connecting member, thereby forming a flexible, linearly elongated absorbent wound dressing confining the alginic acid or salt thereof to the wound dressing;

feeding the wound dressing into a wound;

absorbing exudate from the wound into the absorbent members, thereby swelling the absorbent members; and removing the wound dressing from the wound.

2. A method according to claim 1 and further comprising the steps of enclosing bits of alginic acid or a salt thereof inside of bags formed of a non-adherent, fluid transmissive material to form the absorbent members and confine the alginic acid or salt thereof to the wound dressing.

3. A method according to claim 2 and further comprising the step of perforating the bags with perforations of smaller diameter than the bits of alginic acid or salt thereof.

4. A method according to claim 2 and further comprising the step of forming the bags from a hydrophobic material.

5. A method according to claim 4 and further comprising the step of forming the bags from an ethylene/methyl acrylate copolymer.

6. A method according to claim 4 and further comprising the step of forming the bags from low density polyethylene.

7. A method according to claim 2 and further comprising the step of connecting the bags in end-to-end relationship.

8. A method according to claim 2 and further comprising the step of connecting the bags to a string in spaced apart relation along the string.

9. A method according to claim 1 and further comprising the step of directly adhering individual bits of the alginic acid or salt thereof to a string to form the elongated wound dressing.

10. A method according to claim 9 and further comprising the step of spacing the bits apart from each other along the string.

11. A method according to claim 10 wherein the step of adhering the bits to the string comprises threading the bits onto the string.

12. A method according to claim 9 wherein the bits of alginic acid or salt thereof weigh less than 0.1 gm each.

13. A method according to claim 9 and further comprising the step of surrounding at least a portion of the bits and string with a perforated tubular enclosure formed of a fluid transmissive non-adherent substance.

14. A method according to claim 1 wherein the absorbent member is formed of calcium alginate.

15. A method according to claim 1 wherein at least three absorbent members are connected along the connecting member.

16. A method according to claim 2 wherein at least three absorbent members are connected along the connecting member.

17. A method according to claim 9 wherein at least three absorbent members are connected along the connecting member.

* * * * *